United States Patent
Ericson

(10) Patent No.: US 7,534,620 B2
(45) Date of Patent: *May 19, 2009

(54) METHOD AND DEVICE FOR MONITORING PLATELET FUNCTION

(75) Inventor: Daniel G. Ericson, Rochester, MN (US)

(73) Assignee: PlaCor Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/952,328

(22) Filed: Dec. 7, 2007

(65) Prior Publication Data
US 2008/0086045 A1    Apr. 10, 2008

Related U.S. Application Data

(63) Continuation of application No. 11/077,191, filed on Mar. 10, 2005, now Pat. No. 7,309,607, which is a continuation of application No. PCT/US03/28596, filed on Sep. 10, 2003.

(60) Provisional application No. 60/409,377, filed on Sep. 10, 2002.

(51) Int. Cl.
*G01N 33/48* (2006.01)
*G01N 33/86* (2006.01)

(52) U.S. Cl. ............... 436/69; 436/63; 436/148; 436/164; 436/165; 422/68.1; 422/73; 422/82.05; 435/2; 435/287.1

(58) Field of Classification Search ............ 436/52, 436/63, 69, 148, 164, 165, 180; 422/68.1, 422/73, 81, 82.05, 82.09, 82.13; 435/2, 13, 435/287.1
See application file for complete search history.

(56) References Cited

U.S. PATENT DOCUMENTS

| | | | |
|---|---|---|---|
| 3,766,774 A | 10/1973 | Clark | |
| 4,116,635 A | 9/1978 | Jaeger | |
| 4,604,894 A | 8/1986 | Kratzer et al. | |
| 4,659,550 A | 4/1987 | Schildknecht | |
| 4,725,554 A | 2/1988 | Schildknecht | |
| 4,780,418 A | 10/1988 | Kratzer | |

(Continued)

FOREIGN PATENT DOCUMENTS

| | | |
|---|---|---|
| JP | 59-052744 | 3/1984 |
| JP | 07-146291 | 6/1995 |
| WO | WO 03/023390 A2 | 3/2003 |

OTHER PUBLICATIONS

Beythien et al., "In Vitro Model to Test the Thrombogenicity of Coronary Stents," *Thrombosis Research*, 75(6):581-590 (1994).

(Continued)

*Primary Examiner*—Maureen M Wallenhorst
(74) *Attorney, Agent, or Firm*—Popovich, Wiles & O'Connell, P.A.

(57) ABSTRACT

The invention provides a method of monitoring platelet function in a mammal by passing blood removed from the body of the mammal through a passageway to contact an obstruction or irregularity in the passageway to generate a platelet mass in the passageway, and monitoring the flow or composition of the blood in the passageway to detect the platelet mass. The flow and composition change in response to the formation of a platelet mass in the passageway. Devices, articles, and kits for performing the methods are also disclosed.

57 Claims, 4 Drawing Sheets

U.S. PATENT DOCUMENTS

| | | |
|---|---|---|
| 4,788,139 A | 11/1988 | Ryan |
| 5,039,617 A | 8/1991 | McDonald et al. |
| 5,051,239 A | 9/1991 | von der Goltz |
| 5,089,422 A | 2/1992 | Brubaker |
| 5,184,188 A | 2/1993 | Bull et al. |
| 5,266,462 A | 11/1993 | Hemker et al. |
| 5,296,379 A | 3/1994 | Gorog et al. |
| 5,300,779 A | 4/1994 | Hillman et al. |
| 5,302,348 A | 4/1994 | Cusack et al. |
| 5,316,730 A | 5/1994 | Blake et al. |
| 5,325,295 A | 6/1994 | Fratantoni et al. |
| 5,339,830 A | 8/1994 | Blake, III |
| 5,372,946 A | 12/1994 | Cusak et al. |
| 5,432,084 A | 7/1995 | Brubaker |
| 5,455,009 A | 10/1995 | Vogler et al. |
| 5,504,011 A | 4/1996 | Gavin et al. |
| 5,523,238 A | 6/1996 | Varon et al. |
| 5,534,226 A | 7/1996 | Gavin et al. |
| 5,591,403 A | 1/1997 | Gavin et al. |
| 5,599,718 A | 2/1997 | Gorog |
| 5,602,037 A | 2/1997 | Ostgaard et al. |
| 5,612,187 A | 3/1997 | Brubaker |
| 5,646,046 A | 7/1997 | Fischer et al. |
| 5,665,311 A | 9/1997 | Gorog et al. |
| 5,716,796 A | 2/1998 | Bull et al. |
| 5,731,212 A | 3/1998 | Gavin et al. |
| 5,736,404 A | 4/1998 | Yassinzadeh et al. |
| 5,800,781 A | 9/1998 | Gavin et al. |
| 5,854,076 A | 12/1998 | Kundu et al. |
| 5,854,423 A | 12/1998 | Venegas |
| 5,864,017 A | 1/1999 | Brubaker |
| 5,865,749 A | 2/1999 | Doten et al. |
| 5,888,826 A | 3/1999 | Ostgaard et al. |
| D409,758 S | 5/1999 | Warden et al. |
| 5,916,813 A | 6/1999 | Gorog |
| 5,922,551 A | 7/1999 | Durbin et al. |
| 5,925,569 A | 7/1999 | Gorog et al. |
| 5,951,951 A | 9/1999 | Lane et al. |
| 5,958,716 A | 9/1999 | Kundu |
| 5,972,712 A | 10/1999 | Baugh et al. |
| 6,004,819 A | 12/1999 | Gorog et al. |
| 6,010,911 A | 1/2000 | Baugh et al. |
| 6,016,712 A | 1/2000 | Warden et al. |
| 6,043,871 A | 3/2000 | Solen et al. |
| 6,046,051 A | 4/2000 | Jina |
| 6,060,323 A | 5/2000 | Jina |
| 6,066,504 A | 5/2000 | Jina |
| 6,077,233 A | 6/2000 | Blake, III |
| D429,527 S | 8/2000 | Bolam et al. |
| 6,101,449 A | 8/2000 | Givens et al. |
| 6,159,741 A | 12/2000 | Kratzer et al. |
| 6,232,127 B1 | 5/2001 | Lane et al. |
| 6,245,573 B1 | 6/2001 | Spillert |
| 6,319,719 B1 | 11/2001 | Bhullar et al. |
| 6,338,821 B1 | 1/2002 | Jina |
| 6,391,568 B1 | 5/2002 | Schneider et al. |
| 6,406,672 B1 | 6/2002 | Bhullar et al. |
| 6,410,337 B1 | 6/2002 | Brady et al. |
| 6,448,024 B1 | 9/2002 | Bruegger |
| 6,527,744 B1 | 3/2003 | Kriesel et al. |
| 6,541,262 B1 | 4/2003 | Baugh et al. |
| 6,555,064 B2 | 4/2003 | Baugh et al. |
| 6,555,066 B2 | 4/2003 | Baugh et al. |
| 6,555,381 B2 | 4/2003 | Baugh et al. |
| 6,573,104 B2 | 6/2003 | Carr, Jr. et al. |
| D476,747 S | 7/2003 | Savion et al. |
| 6,586,259 B1 | 7/2003 | Mahan et al. |
| 6,613,573 B1 | 9/2003 | Cohen |
| 6,620,310 B1 | 9/2003 | Ohara et al. |
| D480,482 S | 10/2003 | Savion et al. |
| 6,632,678 B2 | 10/2003 | Aiken et al. |
| 6,645,768 B1 | 11/2003 | Tejidor et al. |
| 6,676,902 B2 | 1/2004 | Baugh et al. |
| 6,692,969 B1 | 2/2004 | Berg et al. |
| 7,262,059 B2 * | 8/2007 | Zheng et al. .................. 436/69 |
| 7,309,607 B2 * | 12/2007 | Ericson ....................... 436/69 |
| 2001/0021355 A1 | 9/2001 | Baugh et al. |
| 2002/0028517 A1 | 3/2002 | Brady et al. |
| 2002/0049557 A1 | 4/2002 | Chen |
| 2003/0027235 A1 | 2/2003 | Kraus et al. |
| 2003/0150745 A1 | 8/2003 | Teodorczyk et al. |
| 2003/0211551 A1 | 11/2003 | Mahan et al. |
| 2004/0011672 A1 | 1/2004 | Ohara et al. |
| 2004/0019300 A1 | 1/2004 | Leonard |

OTHER PUBLICATIONS

Giddens et al., "The Role of Fluid Mechanics in the Localization and Detection of Atherosclerosis," *Journal of Biomechanical Engineering*, 115:588-594 (Nov. 1993).

Jilma, "Platelet Function Analyzer (PFA-100): A Tool to Quantify Congenital or Acquired Platelet Dysfunction," *J Lab Clin Med*, 138(3):152-163 (Sep. 2001).

Invitation to Pay Additional Fees and Partial International Search Report for International Application No. PCT/US2006/015565 (7 pages), Oct. 26, 2006.

Search Report for International Application No. PCT/US03/28596 (8 pages), Feb. 27, 2004.

Wuillemin et al., "Evaluation of a Platelet Function Analyser (PFA-100®) in Patients with a Bleeding Tendency," *Swiss Med Weekly*, 132:443-448 (2002).

* cited by examiner

US 7,534,620 B2

METHOD AND DEVICE FOR MONITORING PLATELET FUNCTION

This application is a continuation of U.S. patent application Ser. No. 11/077,191, filed Mar. 10, 2005, now U.S. Pat. No. 7,309,607 B2, issued on Dec. 18, 2007, which is a continuation of International Application No. PCT/US03/28596, filed Sep. 10, 2003, the contents of each of which are hereby incorporated herein by reference. This application claims the benefit of U.S. Provisional Application No. 60/409,377, filed Sep. 10, 2002.

BACKGROUND

Platelets are anucleated cells that are the primary cells responsible for stopping bleeding. Blood platelets are approximately 3 microns in size and circulate in the blood stream as disc shaped cells that upon activation by either tissue injury or exposure to a foreign material undergo physiological changes that lead to aggregate formation at the site of injury or foreign material. Blood platelets circulate at approximately 250,000 to 350,000 platelets per microliter of whole blood. Upon activation, platelets change shape from a disc to a sphere and form pseudopodia elongations.

The normal platelet response to initiate cessation of bleeding is to undergo a shape change, attach to the surface, and release intraplatelet components that act to provide an autocatalytic recruitment of more platelets. With the recruitment of additional platelets, a platelet plug or aggregate mass forms. The aggregate mass evolves from a single platelet of only 3 microns in size to a mass on the order of millimeters in size. The platelet mass additionally recruits and participates with the plasma coagulation proteins. The plasma coagulation proteins undergo a cascade of events involving 13 enzymes and cofactors, which leads to the activation of plasma fibrin to form a fibrin clot.

It is useful here to briefly summarize the biochemical events of hemostasis (the cessation of bleeding). Normal intact endothelium does not initiate or support platelet adhesion (although in certain vascular diseases platelets may adhere to intact endothelium). Vascular injury, however, exposes the endothelial surface and underlying collagen. Following vascular injury, platelets attach to adhesive proteins such as collagen via specific glycoproteins on the platelet surface. This adhesion is followed or accompanied by platelet activation, where platelets undergo a shape change from a disc shape to a spherical shape with extended pseudopodia. At this time, the platelet release reaction also occurs. The platelets release biologically active compounds stored in the cytoplasmic bodies that stimulate platelet activation or are otherwise involved in clotting reactions. These include ADP, serotonin, thromboxane $A_2$, and von Willebrand factor. Thromboxane $A_2$ is a potent inducer of platelet secretion and aggregation. It is formed by the enzyme cyclooxygenase, which is inhibited by aspirin, among other drugs.

Following activation, glycoprotein IIb and IIIa (GPIIbIIIa) receptors on the surface of the platelets undergo a conformational change from a relatively inactive conformation to an activated form. GPIIbIIIa receptors mediate the adhesion of more platelets by adhering to the circulating plasma protein fibrinogen, which serves as a bridging ligand between platelets. The adhesion and aggregation of platelets constitutes primary hemostasis.

Secondary hemostasis stabilizes the platelet mass by forming a fibrin clot. The fibrin clot is the end product of a series of reactions involving plasma proteins. The process is known as blood coagulation. Among the plasma proteins involved are the activated forms of the clotting factors II, VII, IX, X, XI, and XII (the activated forms have an "a" following the Roman numeral, e.g., factor IIa). The activated forms of these proteins are serine proteases.

Fibrin is formed from fibrinogen, a large circulating plasma protein, by specific proteolysis. In the process, the protein thrombin (factor IIa) is consumed. Fibrin monomers next spontaneously associate to form polymers and form a loose reinforcement of the platelet plug. Fibrin polymers are then cross-linked by certain enzymes. The fibrin polymer also traps red cells and white cells to form a finished clot.

Under normal conditions of hemostasis, the individual experiencing bleeding benefits from the ability of platelets to change shape, adhere, spread, release chemical messengers and activators, aggregate, and assemble with fibrin. This series of events stops bleeding at the site of injury and initiates the process of wound healing.

But platelet activation and clot formation can also place a person at risk of pathological cardiovascular events. For example, venous blood clot formation in the legs, a condition known as deep vein thrombosis, creates the risk that the blood clots could embolize (break apart) and result in clot entrapment in the lungs or the brain, causing pulmonary embolisms and stroke-related conditions. Platelet activation and fibrin formation in other locations in some persons create aggregates and small clots in the arterial circulation that can also lead to embolization and strokes.

In addition to age and genetic and lifestyle risk factors, implanted medical devices in the blood stream also place patients at greater risk of clot formation and embolization. Each year, approximately 500,000 heart valves are implanted in the United States. Although biomaterial advancement has somewhat reduced the risk of thrombosis (clot formation), all patients with mechanical heart valves are at increased risk of clot formation, embolization, and stroke.

Arterial stents are another type of device placed in the circulatory system that place patients at risk from platelet activation. Arterial stents are placed in clogged coronary and carotid arteries to provide oxygen to cardiac tissue. They are typically around 5 mm in diameter and are made from stainless steel or other materials. Due to the introduction of a foreign material in the blood stream, platelets can become activated and attach to the wall of the stented vessel. This leads to reocclusion (restenosis) of the stented vessel, which is a very significant risk in patients with arterial stents. Restenosis in the first 28 days is reported in 0.5 to 8% of persons receiving stents.

In an effort to reduce the risk of embolization and restenosis, patients receiving heart valves or arterial stents are commonly placed on anti-coagulant or platelet-inhibiting medications before, during, and after the procedures.

Current platelet inhibiting drugs fall into three groups: (1) aspirin-related drugs, which inhibit the platelet cyclooxygenase enzyme, thus reducing production of thromboxane $A_2$, which is a platelet activator; (2) ADP-receptor inhibiting drugs, which block a surface membrane receptor on the platelets that is involved in the activation process; (3) monoclonal antibodies that block GPIIbIIIa receptors on the platelet surface. The GPIIbIIIa receptor binds the plasma coagulation factor fibrinogen, which is involved in both aggregation and in forming a fibrin clot.

All three approaches are effective in reducing platelet activation, however no intervention is successful on all patients. Aspirin is the least expensive. But the appropriate dose varies unpredictably from person to person, and up to 30% of individuals on long-term aspirin therapy do not achieve inhibition of platelet adhesion. The ADP-inhibiting drugs are more expensive than aspirin, but are gaining popularity. However, as with aspirin, the required dose and duration of therapy varies, and a large variation in platelet adhesion characteristics in patients on the drugs exists. The GPIIbIIIa-inhibiting drugs are argued to provide the greatest platelet inhibition, but they are very expensive and still suffer from patient-to-patient variability in dosing and effectiveness. Other medications are likely to emerge, but all will probably still have the patient-to-patient variability seen with other approaches.

The failure to determine the proper dose and medication to inhibit platelets can have a great cost in money, and can cause unnecessary morbidity and death. For example, patients on anti-GPIIbIIIa drugs have been reported to have from a 5.8 to 11.2% incidence of adverse reactions in the first 28 days after stenting. The adverse reactions were defined as death, myocardial infarction, or urgent need for reintervention with angioplasty procedures. The risk was even higher when patients were not treated with the drugs. (*New England J. Med.* 330:956-961, 1994; *New. England J. Med.* 336:1689-96A, 1997; *Lancet* 349:1429-35, 1997.)

Thus, anti-platelet drugs have a large patient-to-patient variability and many patients are refractory to some anti-platelet drugs. A method is needed to monitor platelet function so the proper dose of an anti-platelet drug for a particular patient can be determined, and so a physician can determine whether a particular patient is refractory to one anti-platelet drug but responsive to another.

No reliable point-of-care method currently exists to specifically determine if platelet adhesion and aggregation have been inhibited. Thus, there is a need for a method and a device to measure platelet function, and preferably to measure platelet adhesion and aggregation as part of the measurement of platelet function. The need to measure platelet function is particularly acute in patients receiving arterial stents or other cardiovascular devices, and in other persons at risk of adverse cardiovascular events. Such a method would allow an attending physician to ensure that platelet function has in fact been inhibited in a patient at risk, and to adjust pharmacologic parameters prior to implanting a cardiovascular device, which will reduce the risk of adverse events associated with platelet initiation of clot formation.

Another need to monitor platelet function arises in platelet transfusions. Platelets are harvested and used in platelet transfusions to support patients at risk of bleeding. However, platelet storage poses problems not found with the storage of whole blood or other components. Whole blood, red and white cells may be stored at 4° C. for weeks. However, platelets will aggregate in cold storage and when allowed to settle. Therefore, the standard means of storing platelets is at room temperature with gentle agitation. Even under these conditions, platelets lose function by about 5 days. Thus, methods and devices for monitoring platelet function are also needed to determine whether stored platelets have adequate activity to be transfused into patients.

Another need to monitor platelet function exists to test patients undergoing a medical or dental procedure for their risk of excessive bleeding during the procedure.

Accordingly, a need exists for a method to measure platelet function. Preferably, the method would monitor platelet adhesion and aggregation. Preferably, the method would monitor platelet function specifically, separately from the other aspects of clotting such as blood coagulation. Preferably, the method would be inexpensive. Preferably, the method would not depend upon platelet activation by any particular chemical platelet activator or group of chemical platelet activators. Preferably, the method could be used on whole, unprocessed blood, and could produce results quickly (e.g., be used at the bedside, during a physician visit, or during a medical procedure to provide a result almost immediately). Devices to monitor platelet function are also needed.

SUMMARY OF THE INVENTION

The invention provides methods and devices for assessing platelet function, as evidenced by platelet adhesion, and preferably platelet aggregation. In the methods, blood is drawn through a passageway, such as a catheter, past or against an obstruction or irregularity in the passageway, such as a wire placed in the catheter. The platelets adhere and aggregate on the obstruction or on the wall of the passageway near the obstruction or irregularity, and form a platelet mass. It is believed that shear forces associated with passing or contacting the obstruction or irregularity in the passageway activate the platelets and induce them to adhere to the foreign material of the obstruction or the walls of passageway and to aggregate. When the plug forms, it occludes the lumen of the passageway and flow stops or slows. The time of partial or full occlusion of the lumen can be recorded as the platelet plug formation time.

Since a plug is the end product of platelet activity, formation of a plug depends on the functioning of all platelet activities, including platelet adhesion and, if the plug is thicker than about 15 microns, platelet aggregation. (If the plug is thicker than about 15 microns, it involves more than a layer of platelets that forms due to platelet adhesion to a surface, but rather involves a mass formed by platelet-to-platelet aggregation.) This contrasts with some current platelet tests that measure only one specific platelet activity, such as release of a particular biochemical, or depend only on platelet adhesion and not aggregation. It has been found that the platelet mass in the methods of the present invention contains little or no fibrin or red or white blood cells. Thus, in at least some embodiments, the methods of the invention measure platelet function specifically, independently of the blood coagulation reactions.

No chemical or biological platelet activators need to be added to the blood or the passageway for the present methods, although in some embodiments they optionally can be added. Thus, the methods do not depend on platelets responding to a particular biochemical activator or particular group of activators. The methods are fast and can use whole unprocessed blood. Accordingly, they can produce results quickly and inexpensively with a small sample of blood taken at the patient's bedside, during a physician visit, or during an interventional procedure.

Thus, the invention provides a method of monitoring platelet function comprising: passing blood removed from a mammal through a passageway comprising an obstruction or an irregularity, to contact the obstruction or the wall of the passageway at the irregularity, to generate a platelet mass in the passageway; and monitoring the flow or composition of the blood in the passageway to detect formation of the platelet mass; wherein the passageway does not comprise an added biological agent that activates platelets.

The invention also provides a method of monitoring platelet function in a mammal comprising: passing blood removed from a mammal through a passageway comprising an obstruction or an irregularity, to contact the obstruction or the wall of the passageway at the irregularity, to generate a platelet mass in the passageway; and monitoring the flow or composition of the blood in the passageway to detect formation of the platelet mass; wherein the platelet mass is substantially depleted in fibrin in comparison to a natural clot.

The invention further provides a device for monitoring platelet function, comprising: (a) a fluid-tight material forming a passageway; (b) a pump functionally linked to the passageway for pumping blood through the passageway; (c) an obstruction within the passageway, arranged such that when blood is pumped through the passageway to contact the obstruction, a platelet mass substantially free of fibrin forms on or near the obstruction; and (d) a means for detecting the flow of blood through the passageway to detect formation of the platelet mass.

The invention further provides a device for monitoring platelet function, comprising: (a) a fluid-tight material forming a passageway; (b) a pump functionally linked to the passageway for pumping blood through the passageway; (c) an obstruction within the passageway, arranged such that when blood is pumped through the passageway to contact the obstruction, a platelet mass substantially free of fibrin forms on or near the obstruction; and (d) a means for detecting the composition of blood in the passageway to detect formation of the platelet mass.

The invention also provides a device for monitoring platelet function, comprising: (a) a fluid-tight material forming a passageway; (b) a pump functionally linked to the passageway for pumping blood through the passageway; wherein the passageway comprises an irregularity arranged such that when blood is pumped through the passageway to contact the wall of the passageway at the irregularity, a platelet mass substantially free of fibrin forms on the wall of the passageway at or near the irregularity; and (c) a means for detecting the flow of blood through the passageway to detect formation of the platelet mass.

The invention also provides a device for monitoring platelet function, comprising: (a) a fluid-tight material forming a passageway; (b) a pump functionally linked to the passageway for pumping blood through the passageway; wherein the passageway comprises an irregularity arranged such that when blood is pumped through the passageway to contact the wall of the passageway at the irregularity, a platelet mass substantially free of fibrin forms on the wall of the passageway at or near the irregularity; and (c) a means for detecting the composition of blood in the passageway to detect formation of the platelet mass.

The invention further provides a device for monitoring platelet function, comprising: (a) a fluid-tight material forming a passageway; (b) a pump functionally linked to the passageway for pumping blood through the passageway; (c) an obstruction within the passageway, arranged such that when blood is pumped through the passageway to contact the obstruction, a platelet mass substantially free of fibrin forms on or near the obstruction; and (d) a blood flow detector to detect formation of the platelet mass.

The invention further provides a device for monitoring platelet function, comprising: (a) a fluid-tight material forming a passageway; (b) a pump functionally linked to the passageway for pumping blood through the passageway; (c) an obstruction within the passageway, arranged such that when blood is pumped through the passageway to contact the obstruction, a platelet mass substantially free of fibrin forms on or near the obstruction; and (d) a blood composition detector to detect formation of the platelet mass.

The invention also provides a device for monitoring platelet function, comprising: (a) a fluid-tight material forming a passageway; (b) a pump functionally linked to the passageway for pumping blood through the passageway; wherein the passageway comprises an irregularity arranged such that when blood is pumped through the passageway to contact the wall of the passageway at the irregularity, a platelet mass substantially free of fibrin forms on the wall of the passageway at or near the irregularity; and (c) a blood flow detector to detect formation of the platelet mass.

The invention also provides a device for monitoring platelet function, comprising: (a) a fluid-tight material forming a passageway; (b) a pump functionally linked to the passageway for pumping blood through the passageway; wherein the passageway comprises an irregularity arranged such that when blood is pumped through the passageway to contact the wall of the passageway at the irregularity, a platelet mass substantially free of fibrin forms on the wall of the passageway at or near the irregularity; and (c) a blood composition detector to detect formation of the platelet mass.

The invention also provides an article for use in a device for monitoring platelet function, the article comprising: a fluid-tight material forming a passageway; and an obstruction in the passageway, arranged such that when blood is pumped through the passageway to contact the obstruction, a platelet mass substantially free of fibrin forms on or near the obstruction.

The invention also provides an article for use in a device for monitoring platelet function, comprising: a fluid-tight material forming a passageway; wherein the passageway comprises an irregularity arranged such that when blood is pumped through the passageway to contact the wall of the passageway at the irregularity, a platelet mass substantially free of fibrin forms on the wall of the passageway at or near the irregularity.

The invention also provides a kit for use in monitoring platelet function, comprising packaging material containing: (a) an article comprising: (i) a fluid-tight material forming a passageway; and (ii) an obstruction in the passageway, arranged such that when blood is pumped through the passageway to contact the obstruction, a platelet mass substantially free of fibrin forms on or near the obstruction; and (b) instruction means indicating the article is to be used in a device for monitoring platelet function.

The invention also provides a kit for use in monitoring platelet function, comprising packaging material containing: (a) an article comprising: a fluid-tight material forming a passageway; wherein the passageway comprises an irregularity arranged such that when blood is pumped through the passageway past the irregularity, a platelet mass substantially free of fibrin forms on the wall of the passageway at or near the irregularity; and (b) instruction means indicating the article is to be used in a device for monitoring platelet function.

DETAILED DESCRIPTION

Definitions

Figure 1A:
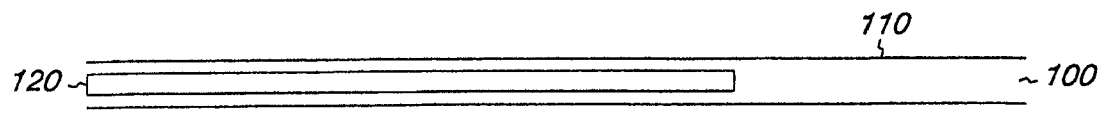
FIGS. 1A-G show passageways for the passage of blood, with various types of obstructions and irregularities in the passageways.

"Platelet function" refers to platelets adhering to a substrate, changing shape, releasing chemical messengers or clotting factors stored in the cytoplasm of the platelets, and/or aggregating with other platelets. "A biological or chemical agent that activates platelets" refers to a substance that upon contact with platelets induces platelets to perform any of those platelet functions (without a requirement that the platelets be exposed to shear or any other mechanical activator).

The term "a biological agent that activates platelets" refers to an agent found naturally in a mammalian body that has the biological role of activating platelets, such as collagen, ADP, thrombin, thromboxane $A_2$, serotonin, and epinephrine.

"A chemical agent that activates platelets" refers to a compound that activates platelets other than a mammalian biological agent. It includes, e.g., non-biological synthetic compounds, derivatives of biological agents that activate platelets, or biological agents found in plants or microorganisms that activate platelets.

"An added biological or chemical agent" refers to a compound or substance that is added to the blood after removal from the body. An "added agent in the passageway" refers to an agent placed or incorporated in the passageway prior to addition of blood to the passageway. The agent could be, for instance, adhered to the wall of the passageway or to an obstruction in the passageway.

"Obstruction" refers to an object that partially or fully obstructs the passageway. Preferably the obstruction partially obstructs the passageway. Examples of obstructions include (a) a plug, such as a wire, that occupies a portion of the passageway (preferably with a space between the plug and the wall of the passageway), (b) a filter or mesh, or (c) a fiber.

As used herein, an obstruction in the passageway that is a "plug" is a solid nonporous object that partially or fully obstructs the passageway. The plug can be any shape in cross-section, e.g., circular, square, or rectangular, and can be composed of any non-porous material, e.g., plastic or metal.

"Blood" as used herein refers to whole blood or to a blood fraction containing platelets. Preferably, blood is removed from the mammal and then passed through the passageway in the methods of the invention without any processing and without the addition of any agents (e.g., anti-coagulants or platelet activators). However, the method will also work with purified platelets or with any blood fraction enriched in platelets or containing platelets. Accordingly, the term "blood" includes platelet-containing plasma, purified platelets, or any blood fraction containing platelets.

The term "whole blood" refers to blood that has not been fractionated.

A "platelet mass" as used herein refers to any mass that is predominantly platelets. The mass can also contain fibrin and other cells. Preferably, it is depleted in fibrin and depleted in other cells as compared to a natural clot. A platelet mass can be less than about 15 microns thick in one or more dimensions, i.e., consisting of a layer of platelets about 5 or fewer platelets thick and formed by platelet adhesion, with little or no platelet-to-platelet aggregation. Preferably, however, the platelet mass is thicker than about 15 microns in all dimensions. The term "platelet plug" is used interchangeably with "platelet mass."

DESCRIPTION

The invention provides a method of monitoring platelet function in a mammal involving passing blood removed from the body of the mammal through a passageway to contact an obstruction or irregularity in the passageway to generate a platelet mass in the passageway, and monitoring the flow or composition of blood in the passageway. The formation of a platelet mass causes a change in the flow or composition of the blood in the passageway, and the change in flow or composition is detected.

In devices of the invention, blood passes through a passageway 100, formed by fluid-tight walls 110 of a foreign material (i.e., any material other than the endothelium of a natural blood vessel). (FIG. 1A). Preferably, the foreign material is a non-biological material. It can be, for instance, any type of plastic, glass, rubber, TEFLON, or metal. Within the passageway is an obstruction or irregularity. A passageway with obstruction 120 is shown in FIG. 1A. The obstruction is also preferably made of a foreign material. It can be porous or non-porous. It can be the same material as the wall of the passageway or a different material.

Blood is pumped through the passageway to contact the obstruction or the wall of the passageway at the irregularity. The obstruction or irregularity creates areas of high shear and low shear for fluids passing through the passageway. It is believed that high shear activates the platelets and areas of low shear allow the platelets to adhere and form a platelet mass. Preferably, the blood is pumped past the obstruction or irregularity, until a platelet mass forms that prevents or resists blood passing. However, the obstruction can totally occlude the passageway, and the irregularity can be a closed end of the passageway, where blood can not pass the obstruction or irregularity. In that case, blood can be passed back and forth against the occluding obstruction or irregularity until a platelet mass forms that is detected.

One example of an obstruction is a wire 120 as shown in FIG. 1A. The obstruction preferably only partially obstructs the passageway. Preferably the obstruction leaves a gap of at least about 20 microns between the obstruction and the passageway wall. Thus, in that case, in order to fully occlude the passageway the platelet mass must be at least about 20 microns thick. To form a mass that size, the platelets must not merely adhere to the surface but must also aggregate to each other. Thus, in this embodiment the method tests the ability of the platelets to show both the activity of adhering and the activity of aggregating.

As blood is pumped past the obstruction 120, a platelet mass is formed on or near the obstruction. Typically, the platelet mass forms at a location of low shear, such as on the end of a wire obstruction. Platelet function can be monitored by measuring the time until partial or full occlusion of the passageway. Occlusion of the passageway can be detected by any suitable means. For instance, a light-emitting diode and a coupled detector can be placed across one point of the passageway to detect passing of the red blood past that point. A pressure transducer can be used to monitor the pressure needed to pump the blood. The passageway can be placed across the light path of a spectrophotometer, so that the spectrophotometer detects (a) the passing of red blood past the light path, (b) an increase in scattering and/or a change in color at the point of the platelet plug as the platelet plug develops, if the light path is positioned to pass through the expected point where the platelet plug forms, or (c) a change in color of the blood outside of the platelet plug associated with the formation of the platelet plug. The time it takes the blood to pass from point A to point B can be measured. Chemical sensors can also be used to measure the concentrations of particular biochemicals that change, either in the blood as a whole or in microenvironments at or near the platelet mass, as the platelet mass forms. For instance, pH, $Mg^{++}$ concentration, $K^+$ concentration, $Na^+$ concentration, $O_2$ concentration, or $CO_2$ concentration can be monitored by sensors and methods known in the art.

The dimensions of the passageway and obstruction or irregularity can be any dimensions suitable, i.e., wide enough to allow blood to pass freely through the passageway until a platelet mass forms, and narrow enough that upon formation of a platelet mass the occlusion of the passageway can be detected. For instance, the passageway can be a millimeter or less in diameter or more than a cm in diameter. A wire obstruction of the passageway can leave, for instance, a gap of about 50 microns with the passageway wall. Other larger and smaller gap sizes and dimensions are also possible.

Blood can be pumped bidirectionally or unidirectionally through the passageway. Pumping the blood bidirectionally, i.e., back and forth past the obstruction or irregularity, has the advantage that it allows a smaller volume of blood to be used. Also, with bidirectional flow, any platelet mass formation time can be measured with a finite amount of blood. With unidirectional flow of blood through a linear passageway that is open at both ends, longer platelet mass formation times will require the use of more blood.

Pumping blood unidirectionally through a closed loop, where the blood can cycle the loop as many times as necessary, has the same advantages as bidirectional flow, namely allowing the use of smaller volumes of blood and allowing measurement of extended plug formation times.

Thus, some embodiments of the devices and methods of the invention allow the use of small volumes of blood to monitor platelet activity. Specifically, in some embodiments, less than about 2 ml, less than about 1 ml, less than about 0.4 ml, less than about 0.2 ml, less than about 0.1 ml, or less than 50 µl is used. In some embodiments, a drop, such as is formed by a finger prick, can be used.

Certain embodiments of the obstruction or irregularity are shown in FIGS. 1A-F. FIG. 1A shows a wire 120 as an obstruction. The wire 120 can be centered or off-center in the passageway. Either or both of the passageway 100 and wire 120 can have non-circular cross-sections. The wire 120 in this embodiment can be replaced with a plug of any non-porous material. The wire can be any length, and can be shorter than it is wide.

Figure 1B:
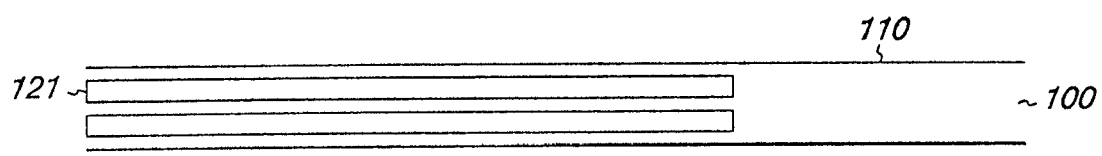

The obstruction can be multiple wires or plugs 121, as shown in FIG. 1B.

Figure 1C:
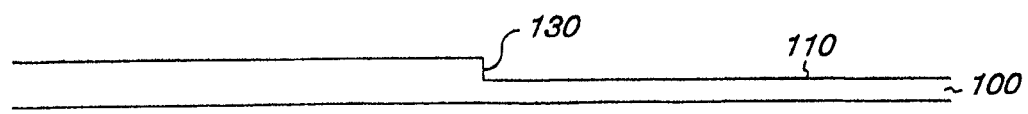

The passageway can comprise an irregularity rather than, or in addition to, an obstruction. The irregularity can be any angle, narrowing, expansion, or curve in the passageway that is suitable to allow formation of a platelet mass. For instance, the irregularity can be step 130 in the wall of the passageway, as shown in FIG. 1C. The smaller diameter section of the passageway could be on the same center as the larger diameter section, or offset.

Figure 1D:
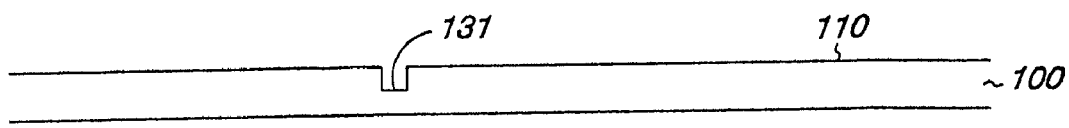
Figure 1E:
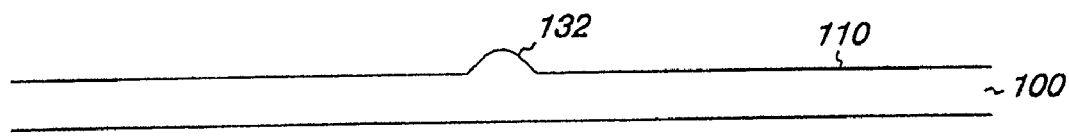

The irregularity could be a narrowed section 131 of the passageway, as shown in FIG. 1D. The irregularity could also be an expansion 132 in the passageway 100 (FIG. 1E).

Figure 1F:
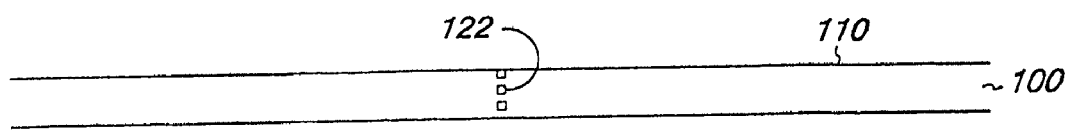
Figure 1G:
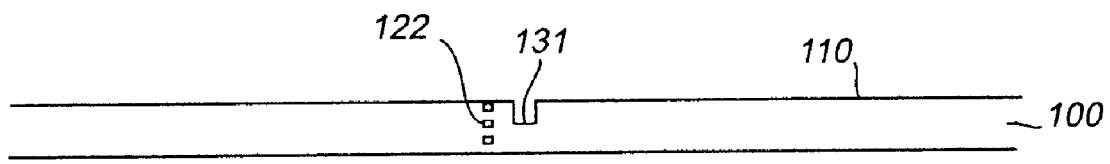

Another example of a suitable obstruction is an inserted flow restrictor 122 (FIG. 1F). The flow restrictor could be, for example, a filter membrane; a single filter or a plurality of fibers, wires, or ribbons; or a piece of woven or knitted fabric.

A plurality of obstructions or irregularities, or a combination of both obstructions and irregularities can be used.

The passageway in the invention can be circular, square, or any other shape in cross-section. The passageway can be curved or linear.

Any flow pattern can be used that produces a platelet mass in a suitable time. For instance, steady unidirectional, or oscillating bidirectional flow can be used. With oscillating bidirectional flow, the oscillation pattern can be sinusoidal, saw tooth, square wave, asymmetric saw tooth, trapezoidal, asymmetric trapezoidal, or other patterns. In unidirectional flow, a pulsate component can be superimposed on the steady flow, and the pulsate component can have any of the above patterns. The flow patterns can also vary with time or with measured resistance to reduce the risk of dislodging a platelet mass once it has started to form. Dwell periods (no flow) can be introduced to allow aggregation of platelets activated by shear.

To achieve the flow patterns described, a pump is preferably used to draw a predetermined volume of blood at a predetermined flow rate (although the flow rate can vary with time, as described above) and a predetermined shear rate into and through the passageway.

Figure 2:
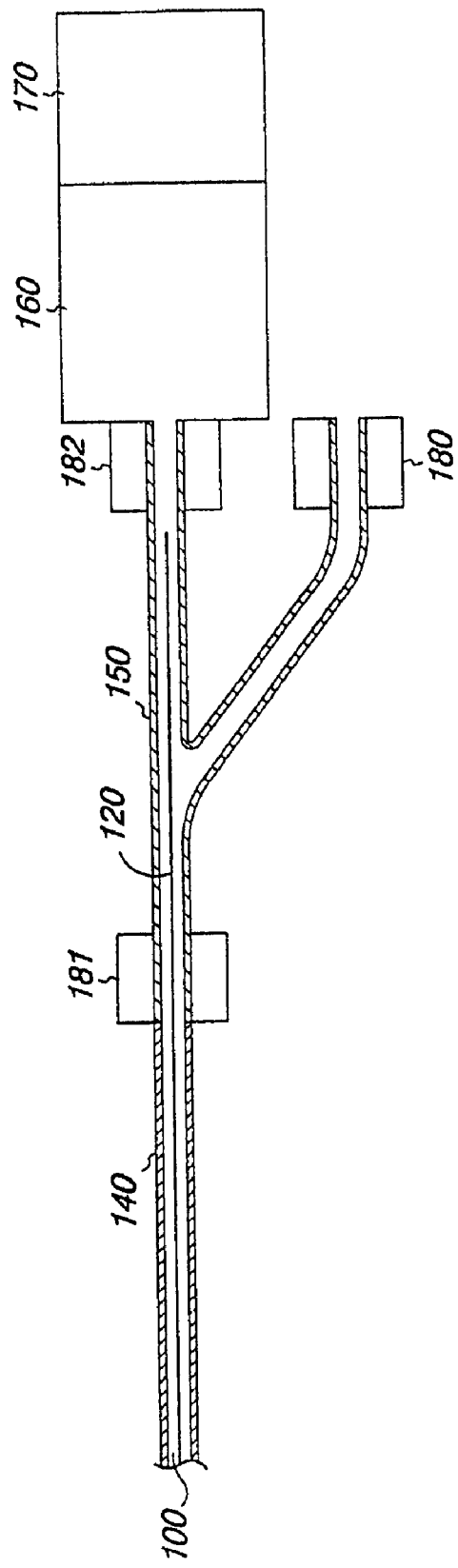
FIG. 2 is a schematic drawing of a device of the invention.

An example of a device for monitoring platelet function of the invention is shown in FIG. 2. A three-way y-shaped flow divider 150 with three luer locks 180, 181, and 182 at its openings is linked to a tube 140 at luer lock 181 to form the passageway 100. The passageway 100 contains wire 120, which is held in position at the open end of the passageway. Blood can be placed in the device by linking a syringe to luer lock 180. Luer lock 182 links the flow divider 150 to a bidirectional pump 160. The bidirectional pump 160 is coupled to a pressure transducer 170 to monitor the pressure in the passageway. After blood is placed in the passageway, the opening at luer lock 180 can be closed. Blood is then pumped back and forth through the passageway until a platelet mass forms, slowing or stopping the flow, as detected by the pressure transducer. The time is recorded as the platelet mass formation time.

One embodiment of an article for use in a device for monitoring platelet function is composed of a rigid precision-molded plastic piece, with a passageway molded therein. The article can have an aperture for accepting blood, linked to the passageway. The ends of the passageway can be open to the air to allow free flow of blood without pressure buildup. The passageway in one embodiment is about a millimeter in diameter and a few cm long, with a stainless steel wire plug of a few millimeters length fixed to one wall of the passageway. The gap between the wire plug and the other wall of the passageway can be, for example, about 50 microns. The article can be placed in a flow detection device, where the device includes a bidirectional pump linked to the passageway and an LED and a coupled detector are placed across one end of the passageway. The detector detects the passing of blood and then air, as the blood is pumped back and forth, until a platelet mass forms and prevents the passing of blood. The article can be made of inexpensive plastic so it is disposable.

One of the advantages of the invention is that no biological or chemical agent that activates platelets must be added to the blood or to the passageway through which blood is pumped. Thus, in some embodiments of the invention, the passageway (prior to addition of blood) does not contain an added biological agent that activates platelets. The blood also optionally does not contain an added biological agent that activates platelets. In some embodiments both the passageway and blood do not have an added biological agent that activates platelets.

In some embodiments, either or both of the passageway and blood do not comprise an added chemical agent that activates platelets.

In some embodiments, the passageway does not comprise a biological component to which platelets naturally adhere.

In specific embodiments, the passageway does not comprise collagen, ADP, epinephrine, or a derivative thereof.

In some embodiments, no biological or chemical agents are added to the removed blood. For instance, in some embodiments, no anti-coagulants are added to the removed blood. In some embodiments, the passageway and blood do not comprise an added anti-coagulant.

However, the methods optionally can also involve use of an added agent that activates platelets. The agent can be added to the blood after it is removed from the body of the mammal, or it can be added to the passageway of the device and thus added to the blood as the blood passes through the passageway. For instance, the walls of the passageway, or the walls of an obstruction can be coated with the agent. If the obstruction is a filter, the filter could be soaked in the agent. Among the agents that could be used are thromboxane $A_2$. Aspirin is believed to inhibit platelet function primarily by inhibiting production of thromboxane $A_2$, so in some embodiments of testing the effectiveness of aspirin therapy, it may be useful to add thromboxane $A_2$ to the blood or passageway. In particular, it may be useful to compare the platelet mass formation time with and without thromboxane $A_2$ added to the blood or passageway.

Other agents that can be added to the removed blood or to the passageway in some embodiments include any of the activators of platelets. Among these are ADP, collagen, thrombin, epinephrine, and serotonin. Other compounds that are not platelet activators but are beneficial to plug formation could also be added. These include fibrinogen, fibrin, and von Willebrand factor.

The invention can be used to monitor platelet function of patients treated with ADP inhibitors. Among these drugs are clopidogrel (PLAVIX) and ticlopidine. In the case of patients treated with ADP inhibitors, if a platelet-activating agent is added to the removed blood or the passageway, ADP may be useful as the added agent. In particular, it may be useful to compare the platelet mass formation time with and without ADP added to the blood or passageway.

The invention can also be used to monitor platelet function of patients treated with GPIIbIIIa inhibitors. Among the GPIIbIIIa inhibitors are Tirofiban, Eptifibatide, and Abciximab. In the case of patients treated with GPIIbIIIa inhibitors, if a platelet-activating agent is added to the removed blood or the passageway, fibrinogen may be a preferred agent since it binds to the GPIIbIIIa receptors.

Thus, the invention also provides a method of monitoring platelet function comprising: (a) passing blood removed from a mammal through a passageway comprising an obstruction or irregularity to contact the obstruction or the wall of the passageway at the irregularity, to generate a platelet mass in the passageway; and monitoring the flow or composition of the blood in the passageway to determine a platelet mass formation time, wherein the blood and passageway do not comprise an added biological or chemical agent that activates platelets; and (b) passing blood removed from a mammal through a passageway comprising an obstruction or irregularity to contact the obstruction or the wall of the passageway at the irregularity, to generate a platelet mass in the passageway; and monitoring the flow or composition of the blood in the passageway to determine a platelet mass formation time, wherein the blood and passageway comprise an added biological or chemical agent that activates platelets; and (c) comparing the platelet mass formation times.

The biological or chemical agent that activates platelets can be, for instance, thromboxane $A_2$, ADP, or fibrinogen.

It has been found that the platelet mass formed in some embodiments of the invention is substantially free of fibrin and of red and white blood cells. Thus, in some embodiments, the platelet mass is substantially depleted in fibrin in comparison to a natural clot. For instance, the platelet mass can contain less than about 50%, less than about 30%, less than about 10%, or less than about 5% of the fibrin per unit mass found in a natural clot in the peripheral blood system. In other embodiments, the platelet mass has no detectable fibrin. In certain embodiments, the platelet mass is substantially depleted in red cells and/or white cells (e.g., contains less than about 50%, less than about 30%, less than about 10%, or less than about 5% of the red or white cell found in a natural clot in the peripheral blood stream or has no detectable red or white cells).

In some embodiments of the invention the blood passes (e.g., is pumped past) the obstruction or irregularity in the passageway.

Platelet mass formation can be detected by monitoring the flow or the composition of the blood in the passageway. In some embodiments, the flow is monitored. Flow can be monitored, for instance, by monitoring the pressure of the blood in the passageway or optically. The pressure can be monitored with a pressure transducer. Optical monitoring can be, for instance, with a LED and a coupled light detector. The optical monitoring, or other methods, can be used to measure the time for blood to travel a certain distance in the passageway. Flow can also be monitored by a flow meter or by volume displacement, as well as by other means known to those of skill in the art.

In some embodiments, the composition of the blood in the passageway is monitored. For instance, formation or size of the platelet mass can be directly monitored, e.g., by optical means such as with an LED or a spectrophotometer. The chemical composition of the blood can also be monitored. For instance, pH or concentration of $O_2$, $CO_2$, $Mg^{++}$, or $K^+$ can be monitored, as these correlate with platelet mass formation.

In some embodiments, the passageway comprises an obstruction. The obstruction can be, for instance, a plug. The plug can be a metal wire, plastic, ceramic, glass, or any non-porous substance. The plug can fully or partially obstruct the passageway.

In some embodiments the platelet mass develops thickness in all dimensions. That is, these embodiments of the methods require platelet aggregation in addition to platelet adhesion. Thus, in some embodiments, the platelet mass has a thickness in all dimensions of at least about 20 microns, at least about 30 microns, at least about 40 microns, at least about 50 microns, at least about 70 microns, or at least about 100 microns.

In some embodiments of the invention, the passageway does not comprise a biological component to which platelets naturally adhere.

In some embodiments, the passageway does not comprise collagen, ADP, epinephrine, or a derivative thereof.

In some embodiments, the passageway and blood do not comprise an added anti-coagulant.

In some embodiments of the methods, the method further comprises adding a platelet activator to the blood. In some embodiments the passageway comprises a platelet activator. The platelet activator can be, for instance, thromboxane $A_2$.

In some embodiments of the methods and devices of the invention, the platelets are activated at least partially by mechanical forces. In some embodiments, the platelets are activated solely by mechanical forces. It is believed that the platelets in the methods of the invention are activated by high shear and adhere at a point of low shear. However, by varying the dimensions of the passageway, the velocity of flow generated by the blood pumping, and the material of the walls of the passageway and of any obstructions (e.g., the adhesiveness of the material), wide ranges of shear can be used. Maximum shear rates in different devices in which platelet mass formation was detected spanned at least the range of 50 to 5,000 $sec^{-1}$.

In some embodiments, less than 2 ml, less than 1 ml, less than 0.4 ml, less than 0.2 ml, less than 0.1 ml, or less than 50 µl of blood is removed from the body of the mammal. In some embodiments, less than these amounts are transferred to the passageway.

In some embodiments of the invention, the blood passes bidirectionally through the passageway. In other embodiments, at least part of the passageway is a loop (i.e., a closed circuit, whether circular, oval, square, or another shape) and the blood passes unidirectionally through the loop.

In some embodiments of the invention, the blood is whole blood. In some embodiments, the removed blood is fractionated before being used in the methods and devices of the invention.

In some embodiments of the devices and articles of the invention, the device or article further comprises a fluid-tight material forming an aperture linked to the passageway.

In some embodiments of the devices of the invention, the device operates without a biological agent that activates platelets. In some embodiments, the device operates without a chemical agent that activates platelets.

In some embodiments of the devices and articles of the invention, the obstruction in the passageway is arranged such that when blood is pumped through the passageway to contact the obstruction, a platelet mass that is substantially free of fibrin and is at least about 20 micron thick in all dimensions forms on or near the obstruction.

In some embodiments of the devices and articles of the invention, the irregularity in the passageway is arranged such that when blood is pumped through the passageway to contact the wall of the passageway at the irregularity, a platelet mass that is substantially free of fibrin and that is at least about 20 micron thick in all dimensions forms on the wall of the passageway at or near the irregularity.

In some embodiments, the blood flows past the obstruction or irregularity, and the obstruction or irregularity leaves a passageway at least 20 microns in diameter or width at the obstruction or irregularity. For instance, the gap between a plug and the wall of the passageway is at least 20 microns in these embodiments. For another example, the diameter or width of the passageway at the narrowest point of the passageway at an irregularity that narrows the passageway is at least 20 microns in these embodiments. When a platelet plug forms that fills the passageway at this point, the passageway is occluded and this is detected as a change in the flow of the blood in the passageway. Thus, the method detects the formation of a platelet plug at least 20 microns thick. In other embodiments, the obstruction or irregularity leaves a passageway of at least 50 microns, at least 100 microns, 20 to 100 microns, or 20 to 200 microns in diameter or width at the obstruction or irregularity.

In some embodiments of the invention, the mammal whose platelet function is monitored is treated with an anti-platelet agent. In particular embodiments, the anti-platelet agent comprises a cyclooxygenase inhibitor (e.g., aspirin or other salicylates), an ADP inhibitor, a GPIIbIIIa inhibitor, or a combination thereof.

Several uses of the methods and devices of the invention exist. The methods and devices can be used to monitor the effectiveness of anti-platelet agents in patients treated with anti-platelet agents. Such patients include those treated by interventional cardiology catheterization. This includes angiograms, angioplasty, and stent placement. In addition, the methods can be used to monitor the effectiveness of anti-platelet agents in patients who receive an artificial heart valve.

The methods and devices can be used to monitor the effectiveness of aspirin or other anti-platelet agents in patients taking the agents to prevent a cardiovascular event, such as coronary thrombosis (heart attack), pulmonary embolism, stroke, or deep vein thrombosis due to excessive platelet activity.

The methods and devices can be used to test patients for their risk of excessive bleeding. This testing can be needed, for instance, prior to a surgical or dental procedure. For instance, the methods can be used on patients prior to having a tooth pulled or wisdom tooth removed to determine their risk of excessive bleeding. If it is determined that the patient is at risk of excessive bleeding, appropriate precautions can be taken, such as doing the procedure in a setting where a blood transfusion or platelet transfusion is available.

The methods can also be used to monitor liver function. When liver function falls, blood flow through the spleen increases. The spleen, which normally degrades old non-functional platelets, then begins to degrade good platelets as well and the platelet count falls. Since a fall in platelet function can be due to low platelet count, by detecting low platelet function the present methods provide a quick way of detecting possible low platelet count. Accordingly, they can be used to screen for liver disease including hepatitis A, B, and C, cirrhosis, and liver damage due to alcoholism.

The invention will now be illustrated by the following non-limiting examples.

EXAMPLES

Example 1

Characterization of Platelet Mass Adhering to Wire in a Tube

Methods:

Platelet mass formation. Human blood was pumped through the lumen of a TEFLON tube with a 24 gauge stainless steel wire in the lumen of the tube, the wire being held in place at the end of the tube. Twenty microliters of blood was pumped in a cycle of 35 seconds at a flow rate of 20/35=1.75 microliters per second. The flow corresponded to a peak shear rate of 1600 $\sec^{-1}$. Following formation of the platelet mass on the end of the wire, the wire and attached platelet mass were rinsed in 0.9% PBS for 5 minutes, then fixed in 1% glutaraldehyde for 3 hours.

Antibody staining. The fluorescein-conjugated monoclonal antibody CD45 (Becton Dickinson) is specific for the surface receptor GPIb, which is found on platelets and not on other blood cells. Ten microliters of the fluorescent antibody was added to the mass on the tip of the wire and incubated in the dark at room temperature for 30 minutes. Non-specifically bound monoclonal antibody was removed from the sample with five 5-minute washes with 0.9% PBS. Fluorescent microscopy was then performed.

Electron microscopy. In another experiment, the mass attached at the end of the wire and fixed with glutaraldehyde was characterized by transmission electron microscopy. The wire and mass were mounted in embedding solution, and cross-sections of the mass were cut using standard sectioning procedures. The cross-sections were evaluated by transmission electron microscopy.

Results:

Fluorescent microscopy showed uniform staining of the mass on the end of the wire with the platelet-specific antibody, with deeper color at points where the mass was deeper. (Data not shown.) This shows the mass consisted largely of platelets, and that platelets were uniformly distributed in the mass.

Electron microscopy showed that the mass consisted only of small anucleated cells (i.e., platelets). No cells containing nuclei (i.e., white blood cells) were seen. In addition, no larger anucleated cells (red blood cells) were identified. Additionally, no fibrin strands were visible in the samples viewed by transmission electron microscopy. Thus, the mass produced by this device on the end of the wire was a platelet mass that was free of fibrin and appeared to be free of other blood cells.

Example 2

Monitoring Platelet Activity in Pigs Receiving Aspirin

Methods:

Pigs were placed on various platelet inhibitors and then the platelet function of the pigs was monitored. Twenty-five pigs received 300 mg aspirin daily for seven days. Ten pigs received 300 mg ticlopidine (an ADP inhibitor) daily. Ten pigs received a combination of 300 mg aspirin and 300 mg ticlopidine daily.

Arterial blood was drawn and placed in a device similar to the device shown in FIG. 2. Twenty microliters of blood were drawn into the lumen of the tube at a rate of 1.0 microliter per second. The wire was 0.016 inches in diameter and the inner diameter of the tube was 0.034 inches in diameter. Blood (20 µl) was delivered via a three-way flow divider (a Touhy-Borst Connector) into a TEFLON tube 2 inches long with a stainless steel wire 0.16 inches in diameter inserted through the tube and extending about three-fourths of the length of the tube. The wire was held in place at the end of the tube. The tube was coupled to a Hamilton syringe pump and to a HP blood pressure transducer for measuring the pressure in the tube. The platelet plug formation time was determined as damping of the blood pressure signal.

Results:

The results are shown in Tables 1-3 below.

TABLE 1

Platelet plug formation time of pigs receiving aspirin.

| Day | Mean platelet plug time (minutes) |
| --- | --- |
| Before aspirin | 3.25 (±0.35) |
| After 3 days | 3.9 (±0.25) |
| After 7 days | 4.6 (±0.42) |

TABLE 2

Platelet plug formation time of pigs receiving ticlopidine.

| Day | Mean platelet plug time (minutes) |
| --- | --- |
| Before ticlopidine | 3.31 |
| After 3 days | 5.67 |
| After 7 days | 6.21 |

TABLE 3

Platelet plug formation time of pigs receiving aspirin and ticlopidine.

| Day | Mean platelet plug time (minutes) |
| --- | --- |
| Before treatment | 2.6 |
| After 1 day | 2.6 |
| After 3 days | 2.6 |
| After 7 days | 18.5 |

The results show that the method used allowed detection of a change in platelet function in the pigs in response to both aspirin (a cyclooxygenase inhibitor) and ticlopidine (an ADP inhibitor). Thus, the method successfully monitors response to anti-platelet drugs, and is not specific for a particular type of anti-platelet drug.

All patents, patent documents, and references cited are incorporated by reference.

What is claimed is:

1. A method for monitoring the flow or composition of blood comprising:
    passing whole blood removed from a mammal through a passageway comprising an obstruction in the passageway and a narrowing of the passageway;
    contacting the blood with the obstruction and the narrowing; and
    monitoring the flow or composition of the blood in the passageway,
    wherein the blood passes bidirectionally through the passageway; and
    wherein less than 2 ml of blood is removed from the body of the mammal.

2. The method of claim 1, wherein less than 1 ml of blood is removed from the body of the mammal.

3. The method of claim 1, wherein less than 0.4 ml of blood is removed from the body of the mammal.

4. The method of claim 1, wherein less than 0.2 ml of blood is removed from the body of the mammal.

5. The method of claim 1, wherein less than 0.1 ml of blood is removed from the body of the mammal.

6. The method of claim 1, wherein less than 50 µl of blood is removed from the body of the mammal.

7. The method of claim 6, wherein the blood is removed from the body of the mammal by a finger prick.

8. The method of claim 1, wherein a single drop of blood is removed from the body of the mammal.

9. The method of claim 8, wherein the blood is removed from the body of the mammal by a finger prick.

10. The method of claim 1, wherein the flow of the blood in the passageway is monitored.

11. The method of claim 10, wherein the flow is monitored by monitoring the pressure of the blood in the passageway.

12. The method of claim 11, wherein the pressure is monitored with a pressure transducer.

13. The method of claim 10, wherein the flow is monitored optically.

14. The method of claim 13, wherein the flow is monitored with a light-emitting diode and a light detector.

15. The method of claim 1, wherein the composition of the blood in the passageway is monitored.

16. The method of claim 15, wherein the size of a platelet mass is directly monitored.

17. The method of claim 15, wherein the chemical composition of the blood is monitored.

18. The method of claim 17, wherein at least one of the pH, concentration of $O_2$, concentration of $CO_2$ concentration of $Mg^{++}$, or concentration of $K^+$ is monitored.

19. The method of claim 1, wherein the obstruction is one or more plugs that partially obstruct the passageway.

20. The method of claim 1, wherein no biological or chemical agents are added to the removed blood.

21. The method of claim 1, wherein the passageway and blood do not comprise an added anti-coagulant.

22. The method of claim 1, wherein the obstruction is a wire.

23. The method of claim 1, wherein the obstruction is a filter.

24. The method of claim 1, wherein the obstruction is a mesh.

25. The method of claim 1, wherein the obstruction is a fiber.

26. The method of claim 1, wherein the obstruction is a filter membrane.

27. The method of claim 1, wherein the obstruction is a plurality of fibers.

28. The method of claim 1, wherein the obstruction is a plurality of wires.

29. The method of claim 1, wherein the obstruction is a plurality of ribbons.

30. The method of claim 1, wherein the obstruction is a piece of woven or knitted fabric.

31. A device for monitoring the flow or composition of blood comprising:
 a fluid-tight material forming a passageway comprising an obstruction in the passageway and a narrowing of the passageway;
 a pump functionally linked to the passageway for pumping blood through the passageway; and
 a detector for detecting the flow or composition of blood in the passageway,
 wherein the obstruction and the narrowing are arranged such that when blood is pumped through the passageway, the blood contacts the obstruction and the narrowing.

32. The device of claim 31, wherein the detector detects the flow of blood in the passageway.

33. The device of claim 32, wherein the flow of blood in the passageway is detected by monitoring the pressure of the blood in the passageway.

34. The device of claim 33, wherein the device further comprises a pressure transducer.

35. The device of claim 31, wherein the detector detects the composition of blood in the passageway.

36. The device of claim 35, wherein the composition of blood in the passageway is detected by monitoring at least one of the pH, concentration of $O_2$, concentration of $CO_2$, concentration of $Mg^{++}$, or concentration of $K^+$.

37. The device of claim 31, wherein the pump is capable of pumping blood through the passageway bidirectionally.

38. The device of claim 31, wherein the obstruction and the narrowing are arranged such that when blood is pumped through the passageway, the blood contacts the obstruction and the narrowing and generates a platelet mass in the passageway.

39. The device of claim 38, wherein the platelet mass is substantially depleted in fibrin in comparison to a natural clot.

40. The device of claim 31, wherein the passageway has a volume of less than 2 ml.

41. The device of claim 31, wherein the passageway has a volume of less than 1 ml.

42. The device of claim 31, wherein the passageway has a volume of less than 0.4 ml.

43. The device of claim 31, wherein the passageway has a volume of less than 0.2 ml.

44. The device of claim 31, wherein the passageway has a volume of less than 0.1 ml.

45. The device of claim 31, wherein the passageway has a volume of less than 50 μl ml.

46. The device of claim 31, wherein the obstruction is one or more plugs that partially obstruct the passageway.

47. The device of claim 31, wherein the obstruction is a wire.

48. The device of claim 31, wherein the obstruction is a filter.

49. The device of claim 31, wherein the obstruction is a mesh.

50. The device of claim 31, wherein the obstruction is a fiber.

51. The device of claim 31, wherein the obstruction is a filter membrane.

52. The device of claim 31, wherein the obstruction is a plurality of fibers.

53. The device of claim 31, wherein the obstruction is a plurality of wires.

54. The device of claim 31, wherein the obstruction is a plurality of ribbons.

55. The device of claim 31, wherein the obstruction is a piece of woven or knitted fabric.

56. The device of claim 31, wherein the device operates without a biological or chemical agent that activates platelets.

57. The device of claim 31, wherein the device operates without an anti-coagulant.

* * * * *